United States Patent
Bardsley et al.

(12)
(10) Patent No.: US 6,551,964 B1
(45) Date of Patent: Apr. 22, 2003

(54) USE OF CITRIC ACID DERIVATIVES AS PESTICIDAL ADJUVANTS

(75) Inventors: Richard Andrew Bardsley, Essex (GB); Udo Matthias Bickers, Frankfurt am Main (DE); Geoffrey Gower Briggs, Essex (GB); Shirley Ann Green, Essex (GB); Adrienne Elizabeth Pate, Essex (GB); Erich Friedrich Sanwald, Frankfurt am Main (DE); David Stock, Essex (GB)

(73) Assignee: Bayer Cropscience S.A. (FR)

( * ) Notice: Subject to any disclaimer, the term of this patent is extended or adjusted under 35 U.S.C. 154(b) by 0 days.

(21) Appl. No.: 09/830,046

(22) PCT Filed: Oct. 22, 1999

(86) PCT No.: PCT/GB99/03430

§ 371 (c)(1),
(2), (4) Date: Jul. 20, 2001

(87) PCT Pub. No.: WO00/24253

PCT Pub. Date: May 4, 2000

(30) Foreign Application Priority Data

Oct. 22, 1998 (GB) .............................................. 9823010

(51) Int. Cl.$^7$ ................................................ A01N 25/00
(52) U.S. Cl. ...................................... 504/358; 514/784
(58) Field of Search ........................... 514/784; 504/358

(56) References Cited

FOREIGN PATENT DOCUMENTS

| DE | 2738878 A1 | 9/1978 |
|---|---|---|
| EP | 0579052 A2 | 1/1994 |
| GB | 2002635 A | 2/1979 |
| GB | 2022070 | 12/1999 |
| JP | 52141853 | 5/1979 |
| WO | 9013222 | 11/1990 |
| WO | 9622020 | 7/1996 |
| WO | 9959406 | 11/1999 |
| WO | 0024253 | 5/2000 |

OTHER PUBLICATIONS

Aven, M., et al., The Use of Adjuvants to Enhance the Efficacy of Fungicidal Triazolopyrimidine–containing Compositions, Current Drugs Ltd., (1999).

T. Abe, et al., "Fungicides For Plastic Films", *Chemical Abstracts*, vol. 88, No. 22, May 29, 1978. Abstract of JP 52–141853.

*Primary Examiner*—S. Mark Clardy
(74) *Attorney, Agent, or Firm*—Ostrolenk, Faber, Gerb & Soffen, LLP

(57) ABSTRACT

The invention provides the use as a pesticidal adjuvant of at least one citric acid derivative and compositions containing the derivative, which has a log octanol-water coefficient (log P) of 2.6 to 11 and an equivalent hydrocarbon (EH) value of 29 to 47. The invention has been shown to enhance the efficacy of a range of pesticides.

10 Claims, No Drawings

USE OF CITRIC ACID DERIVATIVES AS PESTICIDAL ADJUVANTS

This application has been filed under 35 USC 371 as the national stage of international application PCT/EB99/03430, filed Oct. 22, 1999.

FIELD OF THE INVENTION

This invention relates to the novel use of citric acid derivatives in association with pesticides and also pesticidal compositions containing citric acid derivatives. In particular, the invention relates to compositions having fungicidal, herbicidal, insecticidal and acaricidal activity.

BACKGROUND OF THE INVENTION

Pesticidal compounds are typically used in the form of compositions containing one or more co-formulants, for example surfactants. For example, WO96/22020 discloses the use in a pesticidal composition of at least one aliphatic mono-, di- or tri-ester, with no mention of citric acid derivatives. WO90/13222 discloses plant-protecting preparations comprising certain citric acid derivatives that are different from those of the present invention. EP 0 579 052 deals with plant-protecting compositions comprising a biocide and an accelerator, for example linear diacid and esters thereof. GB 2 002 635 and DE 27 38 878 disclose pyrethroid-containing insecticidal compositions comprising citric acid esters to reduce the volatility of the active ingredient. JP 52 141853 provides plastic films containing trialkyl acetylcitrate with good resistance to fungus growth. We have found a new group of compounds, not previously used in association with pesticidal compounds, that can be used with advantage in association with pesticidal compounds.

DESCRIPTION

In a first aspect, the invention provides the use as a pesticidal adjuvant of at least one citric acid derivative, which has a log octanol-water coefficient (log P) of 2.6 to 11 (preferably 2.7 to 11, particularly 4 to 10.7, especially 4 to 10.3) and an equivalent hydrocarbon (EH) value of 29 to 47 (preferably 32 to 44).

We have found that the use of citric acid derivatives according to the invention which have little or no pesticidal activity in their own right, surprisingly aid the penetration of the pesticidal compound into the plant or plant tissue, thereby enhancing the efficacy of the pesticide in the pesticidal composition. This enhanced efficacy enables lower application rates. Lower application rates coupled with low toxicity of citric acid derivatives, leads to a reduction in the environmental impact.

In the context of the invention, the term adjuvant is a compound which enhances. the bioactivity of a pesticide, having no bioactivity in its own right.

In accordance with its normal meaning, the term pesticide, pesticidal etc, includes plant growth regulators (PGRs).

Advantageously, we have found that citric acid derivatives used as part of the invention as well as improving penetration of the pesticidal compound into the plant, are also effective solvents or co-solvents for use in pesticidal compositions. Citric acid derivatives are particularly effective in conjunction with those pesticides that are conventionally formulated as emulsifiable concentrates or emulsions in water, i.e. low to intermediate lipophilic pesticides.

Further advantages of citric acid derivatives include their low flash point and negligible odour compared with many other currently used adjuvants.

The log P value (octanol/water partition coefficient) of a compound is a measure of the solubility of the compound in water. The higher the log P the less soluble is the compound. The log P is calculated from the structure of the compound using the "clog P Program" (Pomona CollegeMed Chem Release 3.54, January 1988, provided by Daylight Chemical Information Systems Inc., Claremont, Calif.). The values generated by this program correlate well in general with those determined experimentally by methods well-known to those skilled in the art. Such experimental methods are difficult to apply accurately to compounds within the scope of this invention, and we therefore use the calculated values.

The equivalent hydrocarbon (EH) value of a compound is a measure of the volatility of a compound. The EH value is arrived at by adding the total number of carbon atoms in the molecule, adding five for any hydroxy group, one for any ether group, eight for any carboxyl group, and then adding three for each ester group. It has been found that EH values determined in this way correlate well with actual volatilities.

Preferred citric acid derivatives are those having the general formula (I)

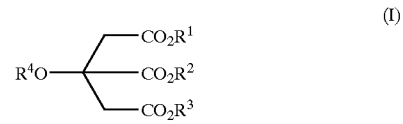

wherein, $R^1$, $R^2$ and $R^3$, which may be the same or different, are $C_1$ to $C_{20}$ alkyl, $C_2$ to $C_{20}$ alkenyl or $C_2$ to $C_{20}$ alkynyl, each of which may be substituted by —$OR^6$, where $R^6$ is hydrogen or alkyl; or hydrogen;

$R^4$ is hydrogen or —C(=O)$R^5$, where $R^5$ is as defined for $R^1$; and $R^1$, $R^2$, $R^3$ and $R^4$ are chosen such that the log P and EH value of the citric acid derivative is as defined hereinabove.

Any alkyl group may be straight or branched and is preferably of 1 to 10 carbon atoms, especially 1 to 7 and particularly 1 to 5 carbon atoms.

Any alkenyl or alkynyl group may be straight or branched and is preferably of 2 to 7 carbon atoms and may contain up to 3 double or triple bonds which may be conjugated, for example vinyl, allyl, butadienyl or propargyl.

Preferably, at least two $R^1$, $R^2$ and $R^3$ groups are not hydrogen.

Preferably $R^1$, $R^2$ and $R^3$, which may be the same or different, are $C_1$ to $C_{20}$ alkyl, especially $C_3$ to $C_8$ alkyl.

Particularly preferred compounds are tri-n-butyl citrate (log P=4.3, EH=32) and O-acetyl tri-n-butyl citrate (log P=4.8, EH=32).

The citric acid derivative of the invention may exist as a single compound, however more commonly it exists as a mixture of compounds. Often, citric acid derivatives are only commercially available as mixtures obtained by fractional distillation. In cases such as these, the log P and EH values are average values.

In a further aspect, the invention provides a pesticidal composition comprising at least one pesticidal compound and at least one citric acid derivative defined hereinabove.

In another aspect, the invention provides a method of combating pests at a locus infested or liable to be infested therewith which comprises applying to said locus an effective amount of a pesticidal composition which comprises a pesticidal compound and at least one citric acid derivative as hereinabove described.

Suitable active ingredients which can be combined with the citric acid derivatives are especially those disclosed in "The Pesticidal Manual", 11th Edition, published by Crop Protection Publications, and may for example be a herbicide, fungicide, insecticide, acaricide or PGR.

A suitable fungicide is for example (i) a conazole sterol $\Delta^{14}$-demethylase inhibitor, (ii) a sterol $\Delta^{14}$-reductase/$\Delta^{8,7}$-isomerase reduction inhibitor based on a 1-[3-(4-tert-butylphenyl)-2-methylpropyl] group which is attached via the N-atom to piperidine or 2,6-dimethylmorpholine (iii) a dithiocarbamate fungicide (iv) a phthalimide fungicide in which a chloroalkylthio group is attached via the N-atom to the optionally hydrogenated phthalimide group.

(v) an anilide fungicide (vi) an mbc fungicide.

(vii) a carbamate fungicide (viii) a copper compound fungicide (ix) a tin compound fungicide (x) a strobilurin type fungicide, (xi) a 2-anilinopyrimidine fungicide (xii) a compound which causes systemic activated resistance, or (xiii) a fungicide selected from the group consisting of chlorothalonil, dimethomorph, fenamidone, fenpiclonil, fluazinam, hymexazol, nuarimol, pencycuron, pyrifenox, thicyofen, probenazole, pyroquilon, tricyclazole, quaternary ammonium compounds, fludioxonil, quinoxyfen, famoxadone, diclocymet, spiroxamine, flumetover, fenhexamid, furametpyr, diflumetorim, fencaramid, carpropamid, sulfur and 5-chloro-6-(2-chloro-6-fluorophenyl)-7-N-(4-methylpiperidin-1-yl)[1,2,4]triazolo[1,5-a] pyrimidine.

Conazoles are defined in ISO standard 257 as compounds based on imidazole or 1,2,4-triazole and containing a halogenated phenyl group. Examples include prochloraz (and its metal complexes—especially the zinc, manganese or copper complex), propiconazole, flusilazole, hexaconazole, tebuconazole, difenoconazole, bromuconazole, cyproconazole, diniconazole, fenbuconazole, imibenconazole, furconazole, tetraconazole, myclobutanil, penconazole, fluquinconazole, azaconazole, imazalil, triflumizole, epoxiconazole, triticonazole, metconazole and oxpoconazole.

Examples of type (ii) fungicides include fenpropimorph and fenpropidin.

Examples of type (iii) fungicides include mancozeb and thiram.

Examples of type (iv) fungicides include folpet, captafol and captan.

Examples of type (v) fungicides include
a) 3',5'-dichloroanilide fungicides in which the anilino nitrogen comprises a ring carrying two oxo substituents, in positions adjacent the nitrogen, e.g. iprodione, vinclozolin or procymidone, or
b) acetanilide fungicides, e.g. metalaxyl or ofurace,
c) sulfanilide fungicides, e.g. dichlofluanid,
d) benzanilide fungicides, e.g. flutolanil, and
e) heteroarylanilide fungicides, e.g. thifluzamide.

Examples of type (vi) fungicides include carbendazim, benomyl and thiophanate-methyl.

Examples of type (vii) fungicides include diethofencarb and propamocarb.

Examples of type (viii) fungicides include Bordeaux mixture, oxine-copper, copper oxychloride and copper naphthenate.

Examples of type (ix) fungicides include tributyltin oxide and tributyltin naphthenate.

Strobilurin type fungicides (type (x) fungicides) are methyl esters or N-methylamides of arylacetic acid in which the acetic acid also carries a methoxymethylene or methoxyimino substituent. The aryl group is usually a 2-substituted phenyl group and/or can be separated from the acetic acid by a linking group such as oxygen. Examples of such compounds are kresoxim-methyl, azoxystrobin, metominostrobin, trifloxystrobin and picoxystrobin.

Examples of type (xi) fungicides include pyrimethanil, mepanipyrim and cyprodinil.

An example of a type (xii) fungicide is that having the code number CGA 2425704, which is sold under the trade name "Bion" and whose proposed common name is acibenzolar.

Examples of herbicides which can be used in conjunction with the citric acid derivatives include
a) Acetolactate synthase inhibitors, e.g.
  (i) sulfonylureas, such as chlorsulfuron, sulfometuron, metsulfuron, bensulfuron, chlorimuron, tribenuron, thifensulfuron, thiameturon, ethametsulfuron, nicosulfuron, rimsulfuron, azimsulfuron, cinosulfuron, prosulfuron, flazasulfuron, pyrazasulfuron, triasulfuron, primisulfuron, oxasulfuron, imazasulfuron, cyclosulfamuron, amidosulfuron, ethoxysulfuron, iodosulfuron, halosulfuron, triflusulfuron, flurpyrsulfuron, sulfosulfuron, foramsulfuron, tritosulfuron, trifloxysulfuron and foramsulfuron,
  (ii) 4,6-dimethoxypyrimidinyloxy benzoic acid analogues, such as, pyrithiobac, bispyribac, pyriminobac and pyribenzoxin;
  (iii) aryisulfonanilides, such as cloransulam, diclosulam, flumetsulam, metosulam and florasulam, and
  (iv) benzenesulfonamides, such as flucarbazone and procarbazone b) choroacetanilides, such as alachlor, metolachlor, acetochlor and propachlor,
c) dinitroanilines, such as trifluralin, pendimethalin and ethalfluralin,
d) HBNs, such as bromoxynil and ioxynil,
e) benzoic acids, such as dicamba and propyzamide,
f) phosphorus acid esters, such as glyphosate, glufosinate and bilanofos,
g) quaternary ammonium compounds, such as paraquat, diqaut and difenzoquat,
h) aryloxyalkanoic acids, such as 2,4-D, 2,4 DB, dichloprop, MCPA, mecoprop, diclofop, clomeprop, fluazifop, haloxyfop, fenoxaprop, quizalofop, propaquizafop, clodinafop and cyhalofop,
i) anilides, such as propanil and mefenacet,
j) protoporphorinogen oxidase inhibitors, e.g.
  (i) diphenyl ethers, such as bifenox, lactofen, acifluorfen, fluoroglycofen, fomesafen, oxyfluorfen, chlomethoxyfen and acloniphen, or
  (ii) 4-chlorophenylazoless, such as, pentoxazone, cinidon-ethyl, flumiclorac, pyraflufen, azafenidin, fluthiacet-methy, sulfentrazone, carfentrazone, isopropazol, profluazol, and
  (iii) flumoxazin, k) ureas, such as chlortoluron, isoproturon, daimuron, iinuron, monolinuron and thidiazuron,
l) uracils, such as bromacil and lenacil,
m) triazines, such as atrazine, simazine, cyananzine, symetryn, terbutryn, trietazine and triaziflam,
n) carbamates, such as desmedipham, phenmedipham, triallate, molinate, dimepiperate, isopropilate, thiobencarb, esprocarm and asulam,
o) pyridines, such as trichlopyr, picloram, diflufenican, fluroxypyr, thiazopyr and clopyralid,
p) pyrazoles, such as pyrazolate, pyrazoxyfen and benzofenap,
q) imidazolidinones, such as imazamethabenz, imazaquin, imazapyr, imazethapyr, imazamox and AC 263222,
r) cyclohexanediones, such as alloxydim, sethoxydim, cycloxydim, tralkoxydim, clethodim and mesotrione,
s) oxa- and thia-diazoles, such as oxadiazon, oxadiardyl and flufenacet, and
t) triazinones, such as, metamitron and metribuzin,
u) miscellaneous compounds, such as isoxaflutole, cinmethylin, bentazon, ethofumesate, metamitron, metribuzin, fluorochloridinone and quinmerac.

Examples of insecticides and acaricides which can be used in conjunction with the citric acid derivates include
a) chlorinated hydrocarbons, such as endosulfan and lindane,
b) nitroimines and cyanoimines, such as imidacloprid, thiamethoxam, thiacloprid and acetamiprid,
c) pyrazoles, such as fipronil, vaniliprole, ethiprole, fenpyroximate, chlofenapyr, tebufenpyrad and tolfenpyrad,
d) tin compouinds, such as fenbutatin and azocyclotin,
e) benzoylureas, such as chlorfluazuron, diflubenzuron, flucycloxuron, teflubenzuron, flufenoxuron, fluazuron, hexaflumuron, lufenuron, triflumuron and novaluron,
f) other ureas, such as hexythiazox, triazamate, diafenthiuiron and sulcofuron,
g) fermentation products, such as ivermectin, abamectin, spinosad, and, emamectin,
h) benzoylhydrazines, such as tebufenozide, halofenozide and methoxyfenozide,
i) carbamates, such as indoxacarb, bendiocarb, carbofuran, carbosulfan, propoxur, methiocarb, aldicarb, methomyl, thiofanox, thiodicarb, pirimicarb and cartap,
j) pyrethroids, e.g.
   (i) esters, such as permethrin, cypermethrin, deltamethrin, cyhalothrin, cyfluthrin, tralomethrin, flumethrin, acrinathrin, fenvalerate, flucythrinate, fluvalinate, ZXI 8901, fenfluthrin, tefluthrin, biphenthrin, transfluthrin, tetramethrin, (including various stereo and/or geometric isomers of these compounds), and
   (ii) non-esters, such as etofenprox, silafluofen, flufenprox, halfenprox and protrifenbute
k) miscellaneous compounds, such as benzoximate, pyridaben, fenoxycarb, pyriproxyfen, hydamethylnon, buprofezin, chinomethionat, clofentezine, acequinocyl, chlofenapyrfenazaquin, pyrimidifen and cyromazine.

Examples of PGRs are chlormequat, paclobutrazol and ethephon.

The names quoted for these compounds are the non-proprietary common names and the chemical structure can be found for example by reference to "The Pesticide Manual" ibid. Structures of compounds not in the Pesticide Manual can be found from the Compendium of Pesticide Common Names (http://www.hclrss.demon.co.uk/).

We have found that the invention is particularly useful with pesticides of high melting point, i.e. greater than 100° C. (especially greater than 130° C.), and/or low: solubility in organic solvents.

The citric acid derivatives of the invention are particularly efficacious with the following fungicides and groups of fungicides:

Conazoles (especially fluquinconazole or triticonazole), strobilurins (especially alkoxyacrylates e.g. azoxystrobin, or those containing an oximeamide moiety) or dimethomorph.

The citric acid derivatives of the invention are particularly efficacious with the following herbicides and groups of herbicides:

Alkyldiaminotriazines (especially triaziflam), aryloxyalkanoic acids and esters (especially fenoxaprop, quizalofop, fluazifop), pyridines (especially fluoroxypyr), carbamates (especially phenmedipham or desmedipham), protoporphoringen oxidase inhibitors (especially carfentrazone), sulfonylureas (especially nicosulfuron), HBNs, cyclohexanediones (especially mesotrione), imidazolidinones (especially imazapyr) and isoxaflutol.

The citric acid derivatives of the invention are particularly efficacious with the following insecticides:

Fipronil, indoxacarb, endosulfan, pirimicarb or clofentezine.

The citric acid derivative is preferably applied at a rate of 20 g to 2000 g, especially 50 g to 500 g, per 100 liters of the diluted formulation.

The citric acid derivative may be incorporated in conventional formulations (e.g. emulsions in water, suspoemulsions or solid formulation types after adsorption onto a suitable inert carrier, such as water dispersible granules) or may be added ("tank-mixed") to the pesticide just prior to use. It may be desirable also to add small quantities of solvent and/or surfactant, especially a non-ionic surfactant, and other additives such as fatty acids to improve the emulsifiability of the citric acid derivative. Typically, the amount of emulsifier is 1 to 20% of the citric acid derivative. The choice of emulsifier is not critical to the performance of the invention, however alcohol ethoxylate surfactants form a preferred group.

The weight ratio of the pesticidal compound to citric acid derivative is preferably 1 to 50, especially 1 to 10.

EXAMPLE

The following Examples show how the pesticidal adjuvants of the invention enhance the efficacy of a variety of pesticidal active ingredients.

Examples 1 and 2 show enhancement of fungicidal efficacy against *Erysiphe graminis* (powdery mildew) and *Plasmopara viticola* respectively.

Example 3 shows enhancement of herbicidal efficacy against a number of common weeds.

Example 4 shows enhancement of insecticidal efficacy against *Aphis fabae*.

Example 5 shows enhancement of insecticidal efficacy against the eggs of *Tetranychus urticae* (red spider mite).

Example 1—Fungicidal Efficacy

In a glasshouse, wheat plants were inoculated with *Erysiphe graminis* (powdery mildew). One day after inoculation, the plants were sprayed with various fungicidal mixtures.

The spray mixtures were prepared by diluting with water a commercial composition of the active ingredient and optionally a solution of the citric acid derivative and emulsifier. When present, the citric acid derivative was either tributyl citrate (TBC) or O-acetyl tributyl citrate (ATBC), and constituted 0.25% w/v of the mixture (see Table A). The solution of citric acid derivative contained 20% emulsifier. The emulsifier was commercially available Synperonic A5 (supplied by Uniqema)

The concentration of active ingredient was selected to give an application rate shown in Table A.

The commercial compositions of the active ingredients used in preparing the spray mixtures are given below.

Fluquinconazole—Commercial composition sold as Castellan

Azoxystrobin—Commercial composition sold as Amistar

Triticonazole—Non-commercial composition formulated in-house to give a 10SC from technical grade triticonazole One week after spraying, the wheat was assessed for control of disease. The results are shown in Table A. The degree of control, shown in the right hand side column, is the average of seven replicates.

TABLE A

| Mix | Active ingredient (Rate g/ha) | Adjuvant | % Control |
|---|---|---|---|
| 1a | Fluquinconazole (250) | nil | 19.6 |
| 2a | Fluquinconazole (250) | TBC | 97.1 |
| 3a | Fluquinconazole (250) | ATBC | 96.1 |
| 4a | Azoxystrobin (250) | nil | 19.6 |
| 5a | Azoxystrobin (250) | TBC | 90.2 |
| 6a | Azoxystrobin (250) | ATBC | 85.3 |
| 7a | Triticonazole (250) | nil | 30.2 |
| 8a | Triticonazole (250) | TBC | 65.1 |
| 9a | Triticonazole (250) | ATBC | 73 |
| 10a | Triticonazole (125) | nil | 24.8 |
| 11a | Triticonazole (125) | TBC | 77.8 |
| 12a | Triticonazole (125) | ATBC | 77.8 |
| 13a | Triticonazole (62.5) | nil | 11.1 |
| 14a | Triticonazole (62.5) | TBC | 63.5 |
| 15a | Triticonazole (62.5) | ATBC | 65.1 |

Example 2—Fungicidal Efficacy

Using the same method as Example 1 vine seedlings were inoculated with *Plasmopara viticola* and sprayed with various mixtures shown in Table B. The spray mixtures were prepared in analogous fashion to Example 1 using dimethomorph as the active ingredient. The commercial composition of dimethomorph used was Forum.

The mixtures were sprayed on to the plants at a rate of 2.5 g of active ingredient per 100 liters of spray mixture.

One week after spraying, the wheat was assessed for control of disease. The results are shown in Table B. The degree of control, shown in the right hand side column, is the average of five replicates.

TABLE B

| Mix | Active ingredient | Adjuvant | % Control |
|---|---|---|---|
| 1b | Dimethomorph | nil | 65.3 |
| 2b | Dimethomorph | TBC | 96.4 |
| 3b | Dimethomorph | ATBC | 72.02 |

Example 3—Herbicidal Efficacy

Seeds of the test species shown in Table C were sown in sandy loam soil and were grown in the glasshouse to the growth stages shown in Table C. Each species was then sprayed with various spray mixtures.

TABLE C

| BROAD-LEAVED | | | GRASSES | | |
|---|---|---|---|---|---|
| Scientific name | Code | Growth Stage | Scientific name | Code | Growth Stage |
| *Amaranthus retroflexus* | AMARE | 11 | *Lokum multiflorum* | LOLMU | 12 |
| *Chenopodium album* | CHEAL | 11 | *Alopecurus myosuriodes* | ALOMY | 12 |
| Stellaria media | STEME | 11–12 | *Echinochloa crus-galli* | ECHCG | 12 |
| *Gallum aparine* | GALAP | 10–11 | *Setaria viridis* | SETVI | 11 |
| *Pharbitis purpurea* | PHBPU | 11–12 | *Digitaria adscendens* | DIGSA | 11–12 |

The spray mixtures were prepared in analogous fashion to Example 1. The active ingredient and citric acid derivative, and the concentration thereof, was selected to give an application rate shown in Table D.

The commercial compositions of the active ingredients used in preparing the spray mixtures are given below.

Carfentrazone—Commercial composition (WG50) sold as Affinity

Triaziflam—Commercial composition (EW30)

Imazethapyr—Commercial composition (EC24) sold as Pursuit.

Nicosulfuron—Commercial composition (SC04) sold as Milagro.

Mesotrione—Non-commercial composition (WP20) made in-house.

Mixtures were sprayed at a rate of 300 liter of spray mixture/hectare. In all cases two replicates were done. After spraying, the sprayed mixture was allowed to dry and the pots were returned to the glasshouse.

The herbicidal effects were assessed visually over a period of 3 weeks. Visual assessment were on a 100% basis (0=no effect compared to untreated plants; 100=complete kill of test species). The results are shown in Table D. Tributyl citrate and O-acetyl tributyl citrate in the absence of any active ingredient caused no herbicidal effects (see experiments 26d to 29d).

TABLE D

| Mix | Active Ingredient (rate kg/ha) | Adjuvant (rate kg/ha) | LOLMU | ALOMY | ECHCG | SETVI | DIGSA | AMARE | CHEAL | STEME | GALAP | PHBPU | MEAN |
|---|---|---|---|---|---|---|---|---|---|---|---|---|---|
| 1d | Carfentrazone (0.02) | nil | 0 | 0 | 0 | 5 | 0 | 80 | 85 | 30 | 70 | 100 | 37 |

TABLE D-continued

| Mix | Active Ingredient (rate kg/ha) | Adjuvant (rate kg/ha) | LOLMU | ALOMY | ECHCG | SETVI | DIGSA | AMARE | CHEAL | STEME | GALAP | PHBPU | MEAN |
|---|---|---|---|---|---|---|---|---|---|---|---|---|---|
| 2d | Carfentrazone (0.02) | ATBC (0.3) | 0 | 0 | 40 | 50 | 0 | 95 | 100 | 10 | 75 | 100 | 47 |
| 3d | Carfentrazone (0.02) | ATBC (0.9) | 0 | 0 | 30 | 45 | 0 | 90 | 90 | 10 | 100 | 100 | 47 |
| 4d | Carfentrazone (0.02) | TBC (0.3) | 0 | 0 | 40 | 55 | 10 | 80 | 95 | 0 | 98 | 100 | 48 |
| 5d | Carfentrazone (0.02) | TBC (0.9) | 0 | 0 | 10 | 50 | 0 | 95 | 90 | 10 | 100 | 100 | 46 |
| 6d | Triaziflam (0.08) | nil | 0 | 10 | 10 | 10 | 0 | 70 | 70 | 10 | 70 | 95 | 31 |
| 7d | Triaziflam (0.08) | ATBC (0.3) | 40 | 40 | 40 | 20 | 10 | 90 | 95 | 10 | 75 | 70 | 49 |
| 8d | Triaziflam (0.08) | ATBC (0.9) | 0 | 30 | 50 | 50 | 0 | 95 | 95 | 20 | 80 | 90 | 51 |
| 9d | Triaziflam (0.08) | TBC (0.3) | 50 | 30 | 50 | 10 | 10 | 80 | 90 | 10 | 60 | 95 | 49 |
| 10d | Triaziflam (0.08) | TBC (0.9) | 10 | 10 | 90 | 20 | 30 | 85 | 95 | 20 | 60 | 98 | 52 |
| 11d | Imazethapyr (0.02) | nil | 0 | 0 | 10 | 40 | 0 | 80 | 30 | 75 | 40 | 15 | 29 |
| 12d | Imazethapyr (0.02) | ATBC (0.3) | 10 | 0 | 80 | 55 | 55 | 75 | 55 | 75 | 40 | 20 | 47 |
| 13d | Imazethapyr (0.02) | ATBC (0.9) | 30 | 20 | 80 | 55 | 50 | 75 | 40 | 70 | 85 | 15 | 52 |
| 14d | Imazethapyr (0.02) | TBC (0.3) | 0 | 10 | 80 | 60 | 55 | 70 | 60 | 80 | 70 | 20 | 51 |
| 15d | Imazethapyr (0.02) | TBC (0.9) | 10 | 0 | 80 | 65 | 50 | 85 | 60 | 80 | 65 | 20 | 52 |
| 16d | Nicosulfuron (0.02) | nil | 0 | 10 | 0 | 10 | 0 | 50 | 5 | 5 | 25 | 0 | 11 |
| 17d | Nicosulfuron (0.02) | ATBC (0.3) | 0 | 10 | 20 | 40 | 0 | 60 | 10 | 0 | 25 | 10 | 18 |
| 18d | Nicosulfuron (0.02) | ATBC (0.9) | 10 | 30 | 40 | 70 | 10 | 60 | 10 | 0 | 40 | 10 | 28 |
| 19d | Nicosulfuron (0.02) | TBC (0.3) | 0 | 10 | 30 | 50 | 0 | 40 | 10 | 0 | 20 | 0 | 16 |
| 20d | Nicosulfuron (0.02) | TBC (0.9) | 0 | 10 | 45 | 50 | 15 | 55 | 10 | 0 | 0 | 15 | 20 |
| 21d | Mesotrione (0.08) | nil | 0 | 0 | 40 | 0 | 30 | 80 | 85 | 85 | 65 | 65 | 45 |
| 22d | Mesotrione (0.08) | ATBC (0.3) | 0 | 5 | 80 | 0 | 75 | 70 | 90 | 70 | 65 | 65 | 52 |
| 23d | Mesotrione (0.08) | ATBC (0.9) | 0 | 25 | 85 | 20 | 80 | 70 | 95 | 73 | 68 | 75 | 59 |
| 24d | Mesotrione (0.08) | TBC (0.3) | 0 | 10 | 85 | 10 | 85 | 70 | 90 | 75 | 63 | 65 | 55 |
| 25d | Mesotrione (0.08) | TBC (0.9) | 0 | 40 | 85 | 20 | 83 | 73 | 90 | 58 | 80 | 70 | 60 |
| 26d | — | ATBC (0.3) | 0 | 0 | 0 | 0 | 0 | 0 | 0 | 0 | 0 | 0 | 0 |
| 27d | — | ATBC (0.9) | 0 | 0 | 0 | 0 | 0 | 0 | 0 | 0 | 0 | 0 | 0 |
| 28d | — | TBC (0.3) | 0 | 0 | 0 | 0 | 0 | 0 | 0 | 0 | 0 | 0 | 0 |
| 29d | — | TBC (0.9) | 0 | 0 | 0 | 0 | 0 | 0 | 0 | 0 | 0 | 0 | 0 |

Example 4—Insecticidal Efficacy

Three-week old bean plants (*Vicia faba*) were sprayed three times to runoff with various mixtures.

The spray mixtures were prepared in analogous fashion to Example 1. The active ingredient and citric acid derivative, and the concentration thereof, was selected to give an application rate shown in Table E. The citric acid derivative was tributyl citrate (TBC).

The commercial compositions of the active ingredients used in preparing the spray mixtures are given below.
Endosulfan—Commercial composition (EC35) sold as Thiodan.
Deltamethrin—Commercial composition (EC2.5) sold as Decis.
Pirimicarb—Commercial composition (SG 50) sold as Pirimor.
Fipronil—Commercial composition (WG80) sold as Regent.

The plants were infested with *Aphis fabae* and the degree of mortality was measured 3 days and 7 days after infestation. The results are shown in columns 4 and 5 of Table E.

In order to test persistency, some of the plants were re-infested 3 days after the first infestation and the degree of mortality was measured 3 and 7 days after re-infestation. The results are shown in columns 6 and 7 of Table E. To test the persistency further, some of the plants were re-infested 7 days after the first infestation and the degree of mortality was measured 3 and 7 days after the second re-infestation. The results are shown in columns 8 and 9 of Table E.

The experiments were conducted at 25° C. and 60% humidity. Each result was the average of two replications.

TABLE E

| Mix | Active ingredient (rate g/ha) | Adj. | Infested @ 0 days | | Reinfested@ 3 days | | Reinfested @ 7 days | |
|---|---|---|---|---|---|---|---|---|
| | | | 3 days | 7 days | 3 days | 7 days | 3 days | 7 days |
| 1e | Endosulfan (10) | nil | 75 | 40 | 15 | 10 | 0 | 0 |
| 2e | Endosulfan (10) | TBC | 98 | 96 | 80 | 63 | 23 | 10 |
| 3e | Endosulfan (3) | nil | 23 | 8 | 0 | 0 | 0 | 0 |
| 4e | Endosulfan (3) | TBC | 88 | 83 | 15 | 0 | 0 | 0 |
| 5e | Endosulfan (1) | nil | 0 | 0 | 0 | 0 | 0 | 0 |
| 6e | Endosulfan (1) | TBC | 20 | 15 | 0 | 0 | 0 | 0 |
| 7e | Deltamethrin (0.03) | nil | 99 | 99 | 98 | 97 | 90 | 80 |
| 8e | Deltamethrin (0.03) | TBC | 100 | 98 | 93 | 92 | 90 | 85 |
| 9e | Deltamethrin (0.01) | nil | 96 | 93 | 80 | 68 | 65 | 30 |
| 10e | Deltamethrin (0.01) | TBC | 97 | 94 | 93 | 88 | 65 | 45 |
| 11e | Deltamethrin (0.003) | nil | 80 | 75 | 15 | 8 | 10 | 0 |
| 12e | Deltamethrin (0.003) | TBC | 78 | 68 | 75 | 58 | 20 | 10 |
| 13e | Pirimicarb (0.3) | nil | 20 | 20 | 0 | 0 | 0 | 0 |
| 14e | Pirimicarb (0.3) | TBC | 83 | 65 | 30 | 15 | 15 | 0 |
| 15e | Pirimicarb (0.1) | nil | 0 | 0 | 0 | 0 | 0 | 0 |
| 16e | Pirimicarb (0.1) | TBC | 25 | 10 | 18 | 0 | 0 | 0 |
| 17e | Fipronil (0.3) | nil | 88 | 85 | 35 | 30 | 0 | 0 |
| 18e | Fipronil (0.3) | TBC | 98 | 98 | 95 | 93 | 85 | 80 |
| 19e | Fipronil (0.1) | nil | 65 | 55 | 15 | 10 | 0 | 0 |
| 20e | Fipronil (0.1) | TBC | 63 | 63 | 65 | 65 | 45 | 40 |

Example 5—Insecticidal (Ovicide) Efficacy

Four week old bean plants were infested with a mixed population of the eggs of *Tetranychus urticae* (red spider mites). After 24 and 48 hours the motile stages were removed with pressurised air. The plants were sprayed to runoff with various spray mixtures.

The spray mixtures were prepared in analogous fashion to Example 1 using clofentezine at rates given in Table F. The citric acid derivative was tributyl citrate (TBC).

The compositions were prepared from commercially available Clofentezine SC 42 (Apollo). The plants were placed in the glass house at 23° C. and 60% humidity.

The mortality of the eggs was assessed after 10 and 14 days. The results are shown in Table F.

TABLE F

| Mix | Active ingredient (Rate g/ha) | Ajuvant | 10 days | 14 days |
|---|---|---|---|---|
| 1f | Clofentezine (10) | nil | 99 | 97 |
| 2f | Clofentezine (10) | TBC | 100 | 100 |
| 3f | Clofentezine (3) | nil | 98 | 95 |
| 4f | Clofentezine (3) | TBC | 100 | 100 |
| 5f | Clofentezine (1) | nil | 70 | 50 |
| 6f | Clofentezine (1) | TBC | 100 | 100 |
| 7f | Clofentezine (0.3) | nil | 40 | 25 |
| 8f | Clofentezine (0.3) | TBC | 70 | 93 |

What is claimed is:

1. A method of enhancing the penetration of a pesticide into a plant or plant tissue comprising applying said pesticide in combination with an adjuvant to said plant or plant tissue infested or liable to be infested by a pest, wherein said adjuvant is a citric acid derivative of the formula (I)

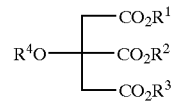

wherein, $R^1$, $R^2$ and $R^3$, which may be the same or different, are $C_1$ to $C_{20}$ alkyl, $C_2$ to $C_{20}$ alkenyl or $C_2$ to $C_{20}$ alkynyl, each of which may be substituted by —$OR^6$, where $R^6$ is hydrogen or alkyl; or hydrogen;

$R^4$ is hydrogen or —$C(=O)R^5$, where $R^5$ is as defined for $R^1$; and wherein $R^1$, $R^2$, $R^3$ and $R^4$ are chosen such that said derivative has a log octanol-water coefficient (log P) of 2.6 to 11 and an equivalent hydrocarbon (EH) value of 29 to 47.

2. The method according to claim 1 where the log P is 2.7 to 11.

3. The method according to claim 2 where the EH is 32 to 34.

4. The method according to claim 3 where the log P is 4 to 10.7.

5. The method according to claim 3 where the log P is 4 to 10.3.

6. The method according to claim 1 where the EH is 32 to 34.

7. The method according to claim 1 where the log P is 4 to 10.7.

8. The method according to claim 1 where the log P is 4 to 10.3.

9. The method according to claim 1 where the pesticide has a melting point greater than 100° C.

10. The method according to claim 9 where the pesticide has a melting point greater than 130° C.

* * * * *